United States Patent [19]

Einars et al.

[11] Patent Number: 5,070,861
[45] Date of Patent: Dec. 10, 1991

[54] X-RAY SIGHTING FOR AIMING LITHOTRIPTER

[75] Inventors: Wolfram Einars, Neukeferloh; Klaus Boehm, Munich; Bernhard Herrmann, Germering; Juergen Neumann, Ailing, all of Fed. Rep. of Germany

[73] Assignee: Dornier Medizintechnik GmbH, Munich, Fed. Rep. of Germany

[21] Appl. No.: 535,719

[22] Filed: Jun. 11, 1990

[30] Foreign Application Priority Data

Jun. 10, 1989 [DE] Fed. Rep. of Germany ....... 3919083

[51] Int. Cl.⁵ .............................................. A61B 17/22
[52] U.S. Cl. ............................. 128/24 OEL; 378/162; 378/205; 128/653.1
[58] Field of Search ...................... 128/24 EL, 653 R; 378/205, 162

[56] References Cited

U.S. PATENT DOCUMENTS

| | | | |
|---|---|---|---|
| 3,609,358 | 9/1971 | Salesi | 378/205 |
| 3,991,310 | 11/1976 | Morrison | 378/205 |
| 4,829,986 | 5/1989 | Eichler et al. | 128/24 EL |
| 4,930,509 | 6/1990 | Brisson | 128/24 EL |

Primary Examiner—Ruth S. Smith
Attorney, Agent, or Firm—R. H. Siegemund

[57] ABSTRACT

A lithotripter has a source for focussed shockwaves and an X-ray device which is mounted for relative displacement and positioning in relation to that source of shockwaves; an improvement includes a device for aiming and sighting in cooperation with the X-ray equipment that includes a carrier element defining a first pair of X-ray contrasting aligned reference points and two additional X-ray contrasting reference points, on a second line and intersecting the first line at a point of intersection at about 15 to 45 degrees; and that aiming and sighting device is mounted in relation to said source of focussed shockwaves such that the point of intersection coincide with a focal point of the shockwave source.

7 Claims, 2 Drawing Sheets

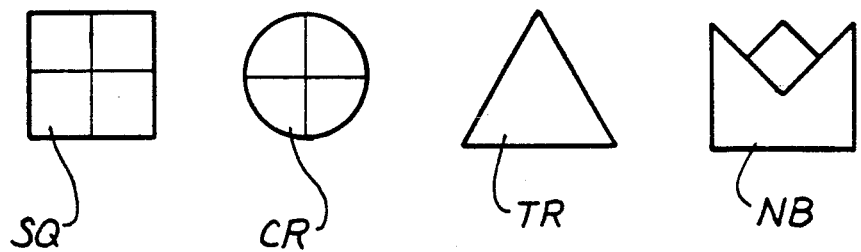
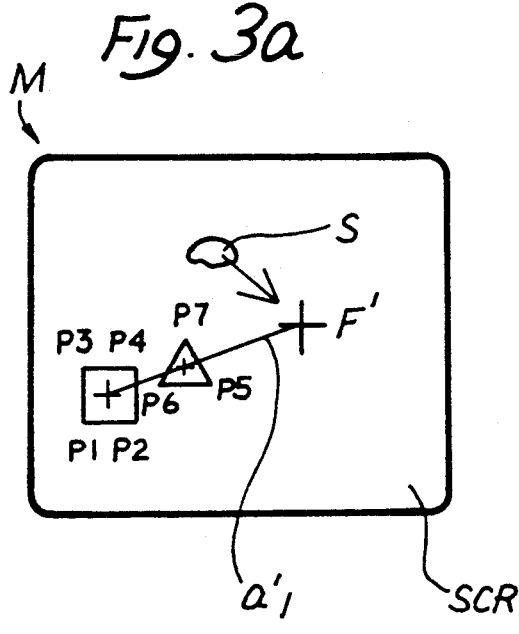
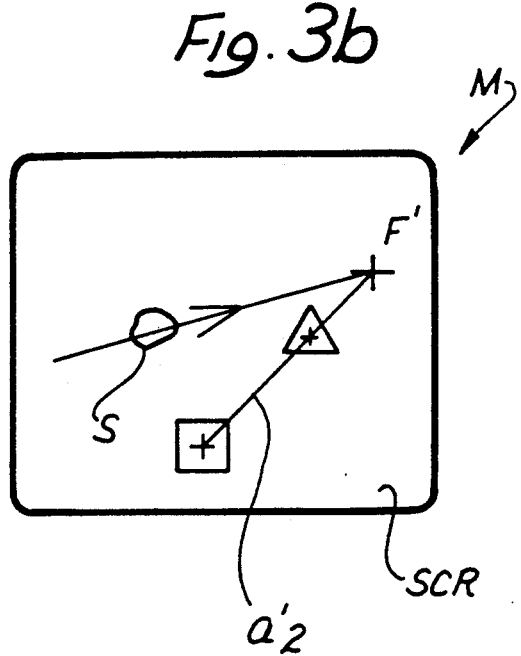

X-RAY SIGHTING FOR AIMING LITHOTRIPTER

BACKGROUND OF THE INVENTION

The present invention relates to X-ray sighting for locating concrements in the body of a human being by means of X-rays for purposes of subsequently treating and comminuting these concrements by means of focused shockwaves under utilization of a lithotripter.

The noninvasive comminution of concrements by means of focused shockwaves requires a very accurately positioning of the patient vis-a-vis the focal point where the shockwaves will attain a very high degree of energy concentration. That concentration must occur only in the concrement and not next to it. For this purpose X-rays and/or locating devices working with ultrasonics are used. The ultrasonic locating process has the advantage of permitting continuous operation because ultrasonic locating does not unduly 'load' the patient. This is quite different in case of X-rays. Here the X-ray load on the patient, particularly in case of a continuous or long lasting exposure is significant and outright dangerous. On the other hand the accuracy of X-rays is greater and not all kinds of concrements can in fact be located by means of ultrasonics.

DESCRIPTION OF THE INVENTION

It is an object of the present invention to provide a new and improved assisting and auxiliary equipment which does permit X-ray locating and positioning of a lithotripter vis-a-vis a concrement, and which when used contributes towards minimizing X-ray exposure to a patient.

It is therefore an object of the present invention to provide a new and improved sighting, aiming and locating equipment for X-ray locating of concrements in the body of a human being for purposes of subsequent exposure of the concrements to focused shockwaves under utilization of a lithotripter.

In accordance with the preferred embodiment of the present invention the objects and features are attained by means of a carrier which is fastenable to the shockwave source and is provided for X-ray negative (permeable) material having inserted at least four X-ray positive (impermeable or contrasting) structures that define geometrically reference points. At least two of these reference points are situated on a first straight line while at least two reference points are situated on a second line which intersects the first line. This aiming and sighting device has these lines positionable to coincide with an X-ray axis and additionally, the aiming and sighting device is fastened to the shockwave source for the lithotripter so that the focal point of the latter coincides with the point of intersection of the two aiming and sighting lines.

The inventive aiming and sighting device is particularly practiced by means of a so called X-ray C carrier element that is a C-shaped carrier having on one end mounted an X-ray tube is mounted and an image amplifier on the opposite end. Equipment of this kind if augmented as per the invention is advantageous because just a few images will in fact suffice to locate a concrement thereby minimizing the X-ray load on the patient. The aiming and sighting device includes a so called X-ray negative material (permeable) which contains, as stated, four X-ray positive (semi-or impermeable to X-rays) members having a geometric contour for delineating reference points. Two of these reference points are situated on one straight line and two of them on the other straight line. These lines intersect in the focused point of the lithotripter.

By means of these four points then, one can position and orient the X-ray C-shaped carrier in two different positions, and this adjustment permits the finding and locating of any concrement. The evaluation is carried out through the principle of aligning points and actually requires no particular skill. The angle between the two sighting and aiming lines is preferably not less than 15 degrees and not more than 45 degrees, the preferred angle being around b 30 degrees. The distance of the two reference points which are on a line is between two and eight inches (5 cm and 20 cm respectively) preferably about 4 inches (10 cm).

X-ray negative material to be used is e.g. synthetic material known Polyoximethylene and traded under the name of DELRIN TM. The carrier as such should not be visible on the monitor screen. The mass distribution perpendicular to the direction of X-ray penetration should be as homogeneous as possible. A hollow element construction is likewise feasible. The outer contour, particularly the side facing the patient, should not be provided with sharp edges or other abrasive parts that could hurt and injure the patient.

The carrier should be fastened to the shockwave source in a rather simple fashion and most certainly should be removable. On the other hand, a stable position is required so that the sighting and aiming device even when put under a mechanical load of about pounds or more will be deformed to a very limited extent, also so that any shift of the aiming line remains under 1 mm.

It should be noted that any load in a mechanical sense can occur simply by kicking the device, or, by being hit by the patient's body. On the other hand, the reference points should be made of X-ray positive material and these "points" are than imaged on the X-ray monitoring screen, at a high contrast. Metal of a high atomic number, i.e. order, such as steel, lead, solder or tin with a high lead content can be used.

The reference points, as far as their geometric contour is concerned, are variable. In a simple fashion they can be a pair of balls or spheres. However a direct aligning arrangement is feasible or square shaped, or triangular ones can be used. These circular, X-ray contrasting bodies may be provided with hairline crossings. Also it may be of advantage if in one particular aiming and targeting line the geometric contour of the two reference figures differ, e.g. a triangle in one instance and a square in the other instance.

In order to reduce the X-ray load on the patient still further, particularly while the C-carrier is adjusted, it might be advisable to put an aperture diaphragm on the targeting device which is affixed in both positions. One can use two diaphragms. In one case a free diaphragm opening is chosen to be about 20 mm and the diaphragms are concentric on the aiming line. The outer diameter is the larger than 10 cm, i.e. larger than 4 inches. The diaphragm material is preferably lead with a thickness of about 3 mm. The diaphragm should be amenable to being folded away or just otherwise removable in a convenient fashion.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 illustrates several contours of reference point figures to be used within the equipment shown in FIG. 1; and FIGS. 3a,b are two different views of an X-ray monitoring screen, for explaining the processing of information obtained by means of the equipment shown in FIGS. 1 and 2.

Proceeding now to the detailed description of the drawings, FIG. 1 illustrates the body B of a patient. The patient rests on a flat rest which is not shown but may be a type shown in a copending application of common assignee, Ser. No. 513,611, filed Apr. 24, 1990. But a rest of the kind shown in U.S. Pat. Nos. 4,705,026 and 4,669,483 can also be used. The X-ray equipment is mounted on a C-shaped carrier; only end portions C1 and C2 of that carrier C are shown. This carrier C includes at end C2 an X-ray tube XT shown in the bottom portion of FIG. 1 while an image amplifier IA is shown at the other end. These two pieces of equipment XT and IA are positioned colinearly to each other and coaxially with reference to the particular axis or line X.

Figure 1:
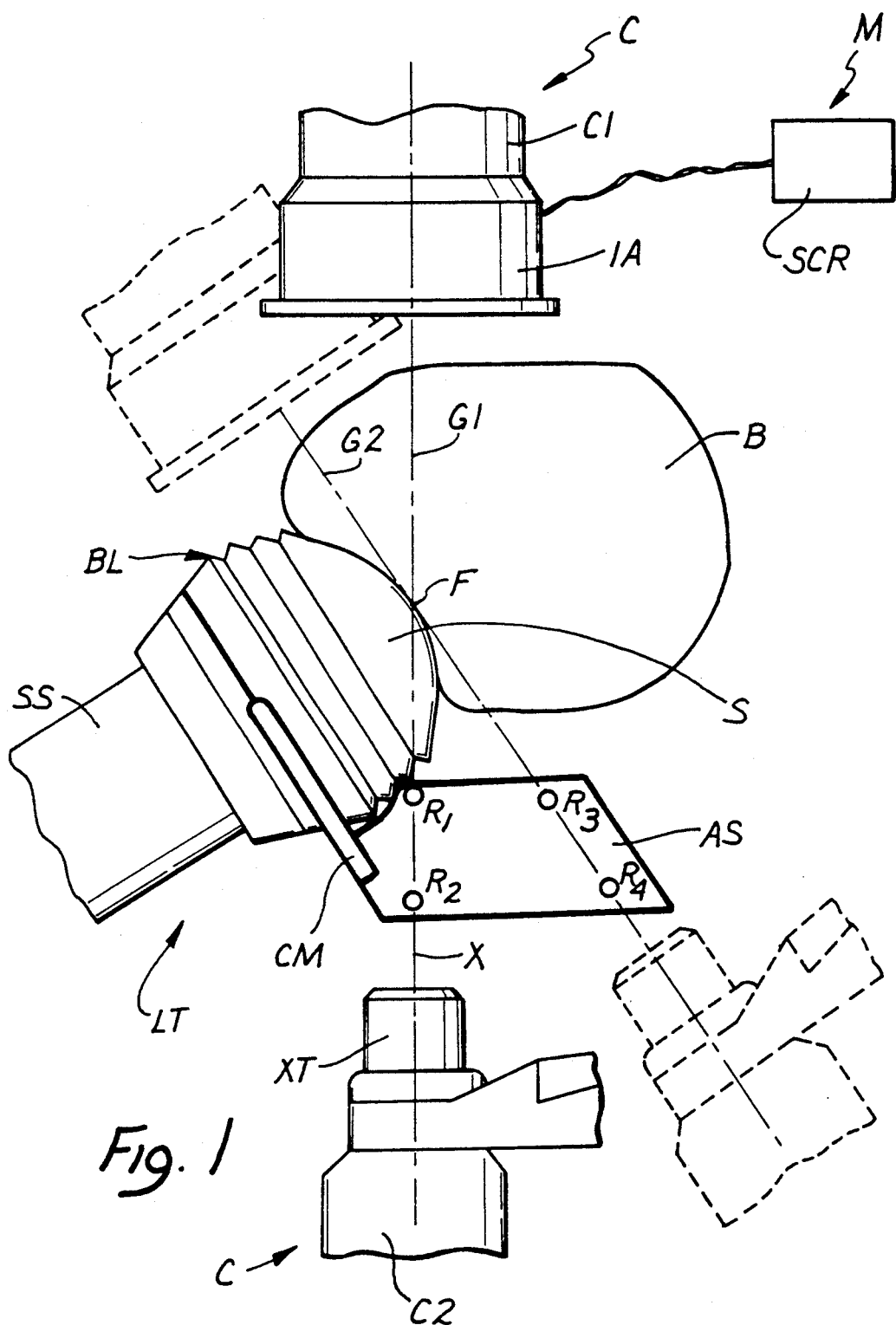
FIG. 1 is a somewhat schematic side view of equipment for practicing the preferred embodiment of the invention in a best mode configuration.

The C-carrier is pivotally mounted for tilting about an axis which runs approximately parallel to the longitudinal axis of the patient body which is essentially transverse to the plane of the drawing of FIG. 1. The tilt axis runs through point F. The pivoting changes the positions as shown in FIG. 1 from the solid line to the dash dot line.

The reference character LT indicates a lithotripter which includes a shockwave source SS of general design having at its front an elastic flexible bellows BL with a surface S which can be urged against the body B of the patient as shown. The lithotripter's shockwave source SS produces focused shockwaves and includes, for example, a rotational ellipsoid with a first focal point in which the spark discharge or the like produces a shockwave which is then reflected to be focused in the second focal point of that rotational ellipsoid. Reference character F denotes that particular focal point.

In addition, an inventive aiming and sighting device AS is provided and includes carrier mount CM by means of which the aiming and sighting device AS is fastened to the lithotripter LT. The device AS is either hollow or filled with or made of a material that is highly permeable to X-rays (X-ray negative). Within that device As, four reference "points" are established. These so called points are actually geometric elements that are highly X-ray absorbing (X-ray positive) and have a geometric contour that defines a point. Examples are shown in FIG. 2.

The two reference points R1 and R2 are situated and placed in device AS to be on a straight G1. A second pair of reference points R3 and R4 is situated to have its points on a second line G2. Moreover the aiming and sighting device AS is fastened and oriented in relation to the lithotripter LT by means of mount CM such that these two lines G1 and G2 intersect in that second focal point F of the lithotripter. In other words and from a point of view of equipment there is the lithotripter LT that produces shockwaves in a focal point F that is thus fixed vis-a-vis that equipment.

In addition the aiming and sighting device is attached to the lithotripter such that the two reference lines G1, G2 being established by the device AS through two pairs of reference points also intersect in that point F. Moreover the entire equipment is such that the axis X between the X-ray source and the X-ray receiver can be made to at least nearly coincide with lines G1 and lines G2, by swivelling or tilting the C-carrier around an axis that runs also through F. Please note, that G1 and G2 are hypothetical lines fixed in position relative to shockwave source SS by virtue of mount CM, while X is the line that runs between X-ray equipment IA and XT and moves with adjustment of carrier C.

X-ray locating of a concrement and relative positioning of lithotripter equipment in relation thereto now proceeds as follows. One begins the aiming operation with a particular position of the lithotripter source LT. The aiming and sighting device AS is secured to the lithotripter in a fashion outlined above. The patient rests with his/her body B on a patient rest and is positioned in a kind of an initial positioning so that in turn the lithotripter (surfaces) is positioned to abut the body B as illustrated. The X-ray carrier C is freely adjustable about F. Preferably suitable markings are provided for attaining these initial positions. In other words, the focal point F and the lines G1, G2, external to AS, and the line X between the two pieces of X-ray equipment, are all hypothetical lines and should in some form be marked on existing physical equipment that contains the elements by means of which these lines are defined and established.

The X-ray direction is given at first through the first reference points R1 and R2. In other words, the carrier C is adjusted so that the X-ray axis X is made to coincide with the line G1. As just stated, a suitable indicating equipment on the outside, may establish information to the personnel so as to be enable them to put these two hypothetical lines X and G1 into coincide position. Now, an X-ray picture is taken wherein the two reference points are or happen to be one directly on top of each other if in fact the initial adjustment was right. More likely, however, they are a little bit off in relation to each other. In other words, the off position of the images on the monitor of the two reference points R1 and R2 from a direct superposition, is an indication of a misalignment of axis X and line G1. Owing, however, to the known distance of R1 from R2, that misalignment can be directly taken from the source as the distance between the two images, because the ratio of distances R1 to R2, to the image point distance is given by the tangential function of that misalignment angle under consideration of any enlarging or reducing factor. This, in turn, means that the shockwave radiation focal point is in fact given by that position because the distance of, say, R1 from F is also a known parameter. The position shockwave source is known and now the position of the X-ray equipment owing to these particular markings is also known. The mutual position can very accurately be determined by way of calculation as stated. If, however, the images of the markings are directly superimposed, then of course that same position marks the position of F on the X-ray monitoring screen SCR.

In addition it has to be considered that a kidney stone or the like is also visible on the X-ray monitor and it is particularly visible in spatial relation to either or both of these images of the reference point markings. Again, from the geometric relations derivable from the X-ray picture one can very accurately determine how much the body of the patient on its rest has to be shifted in order to make the stone coincide with the focus F; at least as far as this one line dimension is concerned. A second X-ray picture will now confirm this adjustment.

In accordance with the second step, X-ray carrier C is pivoted about a particular angle. The angle, of course, is determined by the known angle between the lines G1 and G2. The tilting, hopefully, puts the line X in direct coincidence with the line G2 as identified by the two points R3 and R4 or as near as practicable. In other words, the tilting and positioning of the X-ray equipment should be such that through externally visible markers the X-ray targeting line X coincides with the target defining line G2. Again an X-ray picture is taken and one will see one or both reference point images (now of R3 and R4) as well as another image of the concrement.

Again, the relation of the reference point images to each other determines the focus F so that the position of the concrement can be concluded. The focus is then to be repositioned to coincide with the stone. The patient is going to be shifted again for that purpose so that the concrement will coincide with the line as identified by the two reference marker images. A fourth X-ray picture will be taken, now as the final check to determine whether or not the positioning was carried out successfully. If it was successful, the concrement is now positioned on the second line namely line G2 and the stone is now coinciding with the focal point F of the lithotripter.

FIG. 2 illustrates four possible configurations for reference markers, square SQ, circle CR, triangle TR or an aligned configuration NB. In the latter case, the two reference markers are differently configured. The cross hair illustrated in the square SQ and in the circle CR are inserted, so to speak, with the inclusion of differently contrasting material in the markers. The hair crossing is just an added refinement.

Turning now to FIG. 3a, the locating procedure will be illustrated in greater detail. The monitor screen SC shown illustrates particularly a first position wherein the X-ray source and the X-ray device are situated close to the position shown in FIG. 1 in solid lines. The reference point R2 may here be a square and R1 is a triangle. The picture on the screen SCR shows both as they appear on the monitor. They are slightly off center; but owing to the known geometric relations they have a relation to each other such that the location of the point F' can be calculated as outlined above. The line G!' is now actually the line that would be imaged if it were made of contrast material (which it is not). The monitoring screen also shows an image of a concrement S and now the attending physician can shift the patient and his/her rest until S coincides with F'.

This adjustment can very simply be done manually, but in a more sophisticated equipment there may be a light pen connected to equipment that runs on a program. The physician e.g. touches on the corner points P1,P2,P3,P4 of the square image and subsequently on the three points P5,P6 and P7 of the triangle as imaged. A calculator will then determine the "center of gravity" for each of these figures and will extrapolate a line (G'1) and through simple triangulation it can now calculate and generate a hypothetical position of "image" F' of the focal point on the screen. Having proceeded in this manner, the attending physician will now use a light pen; he will touch with the tip of this light pen the center of the image of stone S, and through a motor operated positioning device the patient is going to be shifted until S in fact coincides with F'. It should be noted that during the entire period of time the X-ray is off, but it may well be advisable to generate a verifying shot.

FIG. 3b shows the screen where in the second position of the X-ray equipment carrier C, shown basically in dotted lines FIG. 1, has been attained and one can see again two reference points which are the reference points R3 and R4. Together they define the hypothetical line image G2 and R4 and again, R4 may be a square and R3 triangle. Visible is also the stone S, and now exactly the same situation is repeated, the point F' is calculated from the relative position of the two images of reference points R3,R4 and then from the screen one can see how much the body of the patient has to be shifted to have the concrement S coincide with the (real) focal point F.

Another possibility of evaluating is that, instead of using a light pen one uses image recognition features or images are processed digitally in order to find the images of the reference points calculating their respective center and the relative position thereof on the monitoring screen, under consideration of the dimensions and imaging size and so forth from which then the position of the focal point is the calculated.

The invention is not limited to the embodiments described above but all changes and modifications thereof, not constituting departing from the spirit and scope of the invention, are intended to be included.

We claim:

1. A lithotripter having a source for focussing shockwaves towards a focal point, further having an X-ray device mounted on a carrier, said carrier being oriented towards the focal point of the source, for relative displacement and for positioning in different positions relative to said focal point, the lithotripter further including a device for aiming and sighting in cooperation with the X-ray device comprising:

a carrier element defining a first pair of X-ray contrasting reference points, said two reference points defining a first line accordingly and further including a second pair of X-ray contrasting reference points, arranged on a second line intersecting said first line in a point of intersection; and means for mounting said carrier element on said source of focused shockwaves such that said point of intersection coincides with said focal point of said shockwave source.

2. A lithotripter as in claim 1, wherein said two lines intersect at an angle between 15 and 45 degrees.

3. A lithotripter as in claim 2, wherein said angle is about 30 degrees.

4. A lithotripter as in claim 1, wherein the distance between the two reference points of each pair is between 5 and 20 cm.

5. A lithotripter as in claim 4, wherein said distance is about 10 cm.

6. A lithotripter as in claim 1, wherein said reference points comprise contrasting geometric configurations selected from the group consisting of square, triangle and circle.

7. A lithotripter as in claim 6, wherein said geometric configurations further comprising X-ray contrasting crosshair lines.

* * * * *